United States Patent
Court

(10) Patent No.: US 9,913,940 B2
(45) Date of Patent: Mar. 13, 2018

(54) ESTABLISHING A WIRELESS COMMUNICATION BETWEEN A FLUID PROCESSING MEDICAL DEVICE AND A MEDICAL ACCESSORY

(71) Applicant: GAMBRO LUNDIA AB, Lund (SE)

(72) Inventor: Thierry Court, Villeurbanne (FR)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 15/519,020

(22) PCT Filed: Oct. 16, 2015

(86) PCT No.: PCT/EP2015/074038
§ 371 (c)(1),
(2) Date: Apr. 13, 2017

(87) PCT Pub. No.: WO2016/059223
PCT Pub. Date: Apr. 21, 2016

(65) Prior Publication Data
US 2017/0239412 A1    Aug. 24, 2017

(30) Foreign Application Priority Data
Oct. 17, 2014    (EP) .................................. 14189409

(51) Int. Cl.
*H04L 29/08*    (2006.01)
*A61M 1/36*    (2006.01)
(Continued)

(52) U.S. Cl.
CPC .............. *A61M 1/367* (2013.01); *A61M 1/16* (2013.01); *G06K 19/06009* (2013.01);
(Continued)

(58) Field of Classification Search
USPC ................................ 235/375; 455/41.1, 41.2
See application file for complete search history.

(56) References Cited

U.S. PATENT DOCUMENTS

2006/0003700 A1*  1/2006  Yasuda ................ H04B 1/3805
                                                                 455/41.2
2006/0242293 A1    10/2006  Russ
(Continued)

FOREIGN PATENT DOCUMENTS

EP         2706726         3/2015
WO    WO 2008/129344    10/2008

OTHER PUBLICATIONS

PCT International Search Report and Written Opinion for PCT/EP2015/074038 dated Dec. 16, 2015 (14 pages).
(Continued)

*Primary Examiner* — Allyson Trail
(74) *Attorney, Agent, or Firm* — Mueting, Raasch & Gebhardt, P.A.

(57) ABSTRACT

A method of establishing a wireless operating communication between the extracorporeal blood treatment device and a medical accessory and extracorporeal blood treatment device configured for implementing the method are provided; the method comprises the steps of establishing a wireless auxiliary communication between the blood treatment device and the medical accessory, transferring configuration data using the wireless auxiliary communication and establishing the wireless operating communication between the blood treatment device and the medical accessory based on the configuration data. A maximum operating distance of the wireless auxiliary communication is shorter than a maximum operating distance of the wireless operating communication.

35 Claims, 4 Drawing Sheets

(51) Int. Cl.
    *H04W 76/02*     (2009.01)
    *H04W 4/00*     (2018.01)
    *H04B 5/00*     (2006.01)
    *A61M 1/16*     (2006.01)
    *G06K 19/06*     (2006.01)

(52) U.S. Cl.
    CPC ........... *H04B 5/0031* (2013.01); *H04L 67/12* (2013.01); *H04W 4/008* (2013.01); *H04W 76/023* (2013.01); *H04W 76/025* (2013.01); *A61M 2205/3592* (2013.01); *A61M 2205/6072* (2013.01)

(56) References Cited

U.S. PATENT DOCUMENTS

| | | | |
|---|---|---|---|
| 2007/0229018 A1 | 10/2007 | Mitchell | |
| 2007/0255116 A1 | 11/2007 | Mehta | |
| 2012/0095381 A1* | 4/2012 | Tonelli | A61M 1/16 604/6.09 |
| 2014/0061306 A1 | 3/2014 | Wu | |
| 2014/0088483 A1* | 3/2014 | Fontanazzi | A61M 1/3639 604/6.09 |
| 2014/0224736 A1* | 8/2014 | Heide | A61M 1/1635 210/646 |
| 2014/0256250 A1* | 9/2014 | Cueto | H04B 5/0031 455/41.1 |
| 2015/0199941 A1* | 7/2015 | Reunamaki | G06F 3/0416 345/174 |
| 2015/0223278 A1* | 8/2015 | Reaston | H04W 4/008 455/41.2 |
| 2015/0254438 A1* | 9/2015 | Odom | G06F 17/30 726/27 |
| 2017/0195827 A1* | 7/2017 | Vasko | H04W 12/08 |

OTHER PUBLICATIONS

European Extended Search Report for Application No. 14189409. 7-1853 dated Apr. 2, 2015 (9 pages).
PCT International Search Report and Written Opinion for PCT/EP2015/073944 dated Jan. 12, 2016 (14 pages).
European Extended Search Report for Application No. 14189408. 9-1951 dated May 7, 2015 (8 pages).
Anonymous "Bar Code Handy Scanner—Denso Wave—Wireless Models", XP-002738544, Jul. 18, 2014.

* cited by examiner

ESTABLISHING A WIRELESS COMMUNICATION BETWEEN A FLUID PROCESSING MEDICAL DEVICE AND A MEDICAL ACCESSORY

This application is a U.S. National Stage Application of International Application No. PCT/EP2015/074038, filed Oct. 16, 2015, which was published in English on Apr. 21, 2016 as International Publication No. WO 2016/059223 A1. International Application No. PCT/EP2015/074038 claims priority to European Application No. 14189409.7 filed Oct. 17, 2014.

The present invention relates to a method for establishing a wireless communication between a fluid processing medical device, particularly a blood treatment device or an infusion pump, and a medical accessory. The present invention further relates to a fluid processing medical system employing the aforementioned method and comprising a fluid processing medical device and a medical accessory. The present invention further relates to a system comprising a plurality of fluid processing medical devices and medical accessories between which wireless communication can be established. Within the scope of the present description, a fluid processing medical device is a medical apparatus including infusion pumps and blood treatment devices, i.e. a medical device configured for treatment of a patient's blood, for example, a medical device comprising a hemofilter, a plasmafilter, a dialyzer, a hemodiafilter, an ultrafilter, and/or other. The fluid processing device may include or be associated to a monitoring apparatus. The monitoring apparatus may be configured to monitor data acquired by the fluid processing apparatus and/or by the medical accessory.

The description refers hereinafter to a blood treatment device, but in general applies equally to any fluid processing medical device, such as for example an infusion pump.

The proposed method facilitates establishing an operating wireless communication between the blood treatment device and the medical accessory by first establishing an auxiliary wireless communication that is used to transfer configuration data necessary for establishing the wireless operating communication. Establishing the wireless auxiliary communication requires the medical accessory to be in proximity to the blood treatment devices, due to the configured maximum operating distance of the wireless auxiliary communication. In detail, a data storage unit comprised in the medical accessory is required to be in proximity to a data acquisition unit comprised in the blood treatment device, since it is these units between which the configuration data necessary for establishing the wireless operating communication is transferred. It is, however, understood that the proximity of the units typically requires the accessory and the device also being in proximity to each other.

The wireless operating communication is configured to provide a secure and reliable data communication having a higher bandwidth and greater maximum operating distance than the wireless auxiliary communication. The invention may provide an easy and reliable mechanism to establish a wireless operating communication. The invention further may provide a safe method for establishing a wireless operating communication, which serves to prevent unintentional wireless communication between a blood treatment device and a medical accessory not configured, designated, and/or suitable for communication with the blood treatment device. The invention may further provide an efficient mechanism for establishing a wireless operating communication without necessitating extensive input of configuration or other data and/or corresponding I/O components (e.g. display, touch panel, keyboard, and/or other). The invention may further provide an efficient mechanism for establishing a wireless operating communication providing improved data safety, effectively reducing the danger of eavesdropping.

BACKGROUND

Generally, wireless data communication between different devices is known and used in different fields of technology. In many fields of technology, it is desirable to replace or avoid wired data communication in order to alleviate the drawbacks usually associated with wired data communication.

Such drawbacks include, for example, that the physical cables or leads required for corresponding connections can pose a safety hazard in that they can interfere with human users operating the connected components. In particular, if many cable connections are present, managing the cables and ensuring that the connections are not inadvertently interrupted can become a cumbersome task. In addition to electric wiring, medical machines such as blood treatment machines can exhibit a number of other similar connections, for example, blood lines and/or medical fluid lines. Consequently, if many connections are present, a disconnection or erroneous connection can pose a more or less critical risk for the treatment and/or the patient.

In some environments, electromagnetic or other interference can negatively affect the wired connections. Additionally, connections between different devices and/or from a device to a wall outlet can restrict the placement of the devices with respect to one another and/or with respect to the outlet or outlets. Consequently, the electrical layout of the environment in which the devices are to be operated has to be configured for operation of the machines. However, often the electrical layout would have to be adapted as the devices change over time and/or if the environment changes (e.g., if the devices have to be moved from one room to another). In most cases, the electrical layout cannot easily be adapted, because of the necessary construction work associated with changes to the internal wiring of a room or building.

Moving devices around might require connections being interrupted and subsequently re-established in that cables need to be unplugged and plugged in again. Common networking connections might additionally require corresponding patching of connections at a central location (i.e. physically disconnecting and re-connecting of patch cables at, for example, a patch panel and/or a network switch).

In case of medical accessories that are designed to, for example, acquire physical data (e.g. pressure, heart rate, temperature, etc.) from a patient before, during, or after treatment, the use of a medical accessory that relies on a wired connection to other components very much restricts the mobility of the patient.

In some cases, while the patient might be restricted in some manner depending upon treatment or medical condition, the use of medical accessories attached to or otherwise carried by the patient might not require any particular restriction. For example, the medical accessory might facilitate monitoring of patient parameters over a longer period of time, in which the patient is generally present within the hospital, without requiring being connected to any particular machine or outlet.

Wireless data connections can alleviate or avoid one or more of the above drawbacks of wired connections, but can entail other drawbacks.

One significant drawback of wireless connections is that wireless connections are typically more difficult to set up than wired connections. In the case of the latter, a user can simply use a suitable cable, identify the two devices to be connected (or one device and a wall outlet), and plug in the connectors located on each end of the cable. Typically, the connectors are configured to connect only to a matching socket in a single manner (e.g. orientation, male/female plugs, color coding, etc.), thereby ensuring a proper connection. In particular, there is very little chance for two devices being connected unintentionally, due to the devices having to be present and the user having to physically identify and connect the devices on-site.

Wireless connections cannot be established in the same way as wired connections, due to the lack of a tangible connection medium. In contrast, the transceiver units integrated into wireless devices have to be programmed and configured to connect with corresponding counterparts, wherein all devices that are intended to participate in wireless data communication with each other have to operate in accordance with the same communication protocols and standards and have to be configured in a manner corresponding to each other (e.g. requiring matching configuration data).

For example, the Wireless Local Area Network (WLAN) IEEE 802.11 standards include media access control (MAC) and physical layer (PHY) specifications for implementing wireless local area network (WLAN) computer communication in the 2.4, 3.6, 5 and 60 GHz frequency bands. In order for a device to establish a data communication using WLAN, corresponding hard- and software components are necessary, as well as a configuration that typically has to be provided upon on-site integration of the device into a WLAN network and/or WLAN ad-hoc connection.

This configuration can include, for example, several technical parameters depending upon the local network configuration. In some examples, a user wishing to integrate a device into a WLAN has to provide the correct Service Set Identifier (SSID) or "network name" the local network has been given, the correct channel (corresponding to a particular frequency or frequency range) that the local network operates on, and—if used—the correct encryption parameters (e.g. a pre-shared key or other credentials) that are required by the encryption standard used (e.g. wired protected access (WPA, WPA2), wired equivalent privacy (WEP), etc.).

Depending upon additional network protocols, the user might have to specify additional networking parameters. For example, if the transmission control protocol/internet protocol (TCP/IP) is used as the transport and network layer, then it might be necessary for the user to provide IP addresses for the device itself, a gateway, a router, one or more name servers (for the domain name system (DNS)), one or more proxies, and/or other devices, as well as further technical parameters (e.g. a subnet mask, etc.).

WO 2008/129344 (A1) describes a method for setting up a fluid treatment apparatus using a single and always accessible reader of information relating to replaceable components, which are to be mounted on the apparatus to perform the fluid treatment. A fluid treatment apparatus having a reader that is always accessible is also described. The reader can also be relied on to enter information other that those relating to the replaceable components, such as commands for the apparatus, patient related information, etc.

One significant factor is that the setting up of a wireless operating communication is a non-trivial task requiring some expertise in the field of wireless communications. Often, medical personnel operating the devices and accessories are not trained to be sufficiently proficient in setting up and running extensive networks of many devices and accessories that are linked in a wireless network. Further, even if the medical personnel were sufficiently proficient, or even if a supporting staff of technicians were available to fulfill such duties, the problem of securing safe operation of the multiple devices and accessories remains. In day to day operations, typically many accessories need to be linked wirelessly to a number of devices, wherein a medical accessory can be, for example, associated to a first patient and linked to a first device (e.g. a blood treatment device) in the morning. Subsequently, the patient has to undergo a different treatment and the wireless operating communication between the medical accessory and the first device is closed and a wireless operating communication to a second device has to be established later in the morning. In the afternoon, the medical accessory can be associated to a second patient undergoing the same or another series of treatments, again requiring several times establishing and closing communication with one or more devices.

All this time it must be ensured that the wireless operating communication is established between the devices and accessories that are actually intended to be linked together. In some cases, a number of blood treatment devices can be located in a single room and a number of patients undergoing blood treatment and each provided with their personal medical accessory (e.g. a pressure cuff) need to be taken care of, requiring being connected to a respective blood treatment device and also requiring the medical accessory being put into wireless operating communication with the respective blood treatment device. It is apparent that a misconfiguration of the wireless operating configuration (e.g., leading to the medical accessory of one patient being mistakenly put into wireless operating communication not with the corresponding blood treatment device, but another one next to the correct one) can lead to potentially disastrous effects for the health of either patient being treated in connection with any of the affected devices and/or accessories. Therefore, it is imperative that a wireless operating communication is established only between the devices and accessories for which the communication is intended.

It is further obvious that the above-described problem affects any device and any accessory potentially connected to a same network—regardless of the location of the device or accessory. Due to the wireless communication and, possibly, a common network providing a supporting infrastructure, a medical accessory can potentially establish a wireless operating communication with any suitable device on the network (e.g. irrespective of the location of the device), such that patient data, treatment data, or any other data can be transmitted on a regular basis and independently from the location of either device/accessory. For example, a physician can collect the history of the blood pressure and other patient parameters over a period of time where the patient is present within a hospital. During this time, the accessory associated with the patient and wirelessly linked to the device used by the physician for his monitoring of the patient's data, can transmit the patient data on a regular basis before, during, and after a treatment session. At the same time, the accessory can be configured to establish a wireless operating communication (also) with a blood treatment device for the period it takes for the patient to undergo a blood treatment session, thereby providing patient data (also) to the blood treatment machine. All this requires that the accessory can be safely configured to establish and close wireless operating connections with different devices.

Another significant factor in setting up wireless devices is that typically the input of the aforementioned configuration data requires corresponding input and output components, for example a display, keyboard, etc. While some devices already necessitate such I/O components for their intended use (e.g. personal computers, tablet computers, etc.), therefore being equipped with these components in any case, some other devices can be operated without the need for any such I/O components designed for user interaction, therefore lacking such I/O components. Some medical accessories can be designed to merely be in data communication with another device in order to take measurements and to transmit the measured value or values taken to the other device without providing a display or a keyboard. A pressure cuff, for example, can be configured to measure the blood pressure of a patient and to communicate the measured values at regular intervals to a blood treatment device. In order for the pressure cuff to operate, full-fledged I/O components are typically not required, except few simple components such as start/stop, on/off, reset, or similar buttons, and/or some indicators (e.g. lamps, LEDs, etc.) indicating an operating status of the pressure cuff.

Even though medical accessories would often very much benefit from a wireless operating communication due to their size and usage properties, the lack of I/O components providing input means allowing for the necessary input of configuration data in order to establish a wireless operating communication often prevents such use and a wired communication is established instead.

Therefore, a mechanism is required that allows for an easy, safe, and efficient way to establish a wireless operating communication between a medical accessory and a medical device, such as a blood treatment device.

SUMMARY OF THE INVENTION

In this situation, it is an object of the invention to provide a mechanism that allows for an easy, safe, and efficient way to establish a secure wireless operating communication between a medical accessory and a medical device.

An auxiliary object is that of providing a mechanism that ensures that a secure wireless operating communication is established only between the medical accessory and the medical device that are intended for connection with each other.

A further object of the invention is to provide a mechanism that allows for continuous data collection, where data can be acquired not only during treatment sessions but also between treatment sessions, when the patient is not associated to a fluid processing device. Data acquired continuously and/or between treatments can be transferred to the fluid processing device and/or a monitoring apparatus as soon as a wireless operating communication has been established. Data acquired by the medical accessory can further be transferred to the fluid processing device and/or a monitoring apparatus during an ongoing treatment and/or otherwise when and as long as a wireless operating communication has been established At least one of the above objects is substantially achieved by a method for establishing a wireless operating communication, a system comprising a medical accessory and a medical device, and a system comprising a plurality of medical accessories and devices according to one or more of the appended claims.

Aspects of the invention are disclosed in the following.

A $1^{st}$ independent aspect of the invention concerns a method of establishing a wireless operating communication between a fluid processing medical device, such as an extracorporeal blood treatment device, and a medical accessory, the method comprising the steps of establishing a wireless auxiliary communication between the fluid processing medical device and the medical accessory; transferring configuration data using the wireless auxiliary communication; and establishing the wireless operating communication between the fluid processing medical device and the medical accessory based on the configuration data, wherein a maximum operating distance of the wireless auxiliary communication is shorter than a maximum operating distance of the wireless operating communication.

In a $2^{nd}$ aspect according to the $1^{st}$ aspect, the maximum operating distance of the wireless auxiliary communication is less than 2 m, preferably the maximum operating distance of the wireless auxiliary communication is equal to or less than 20 cm, more preferably the maximum operating distance of the wireless auxiliary communication is equal to or less than 10 cm.

In a $3^{rd}$ aspect according to anyone of the preceding aspects, the maximum operating distance of the wireless operating communication is equal to or greater than 2 m, preferably the maximum operating distance of the wireless operating communication is equal to or greater than 10 m.

In a $4^{th}$ aspect according to anyone of the preceding aspects, the step of establishing the wireless operating communication further comprises the steps of determining, based on the configuration data, communication data of the medical accessory, the communication data of the medical accessory being configured for operation with the wireless operating communication, the communication data further being indicative of a communication configuration of the medical accessory; initiating, based on the communication data, a data communication between the fluid processing medical device and the medical accessory by means of the wireless operating communication.

In a $5^{th}$ aspect according to anyone of the preceding aspects, the configuration data comprise type data indicative of a plurality of properties of the medical accessory.

In a $6^{th}$ aspect according to the preceding aspect, the step of establishing the wireless operating communication further comprises determining, based on the type data, whether the medical accessory is of a type suitable for operation with the fluid processing medical device; and closing both the wireless auxiliary communication and the wireless operating communication with the medical accessory, if the medical accessory is not of a type suitable for operation with the fluid processing medical device.

In a $7^{th}$ aspect according to the preceding aspect, the plurality of properties of the medical accessory that the type data are indicative of, comprise one or more of: hardware data indicative of a hardware configuration of the medical accessory; software data indicative of a software configuration of the medical accessory; and firmware data indicative of a firmware configuration of the medical accessory, and the step of determining whether the medical accessory is of a type suitable for operation with the fluid processing medical device is based on one or more of the hardware data, the software data, and the firmware data.

In a $8^{th}$ aspect according to anyone of the preceding aspects, after the wireless operating communication has been established, the method further comprises the steps of establishing a second wireless auxiliary communication between the fluid processing medical device and a second medical accessory; transferring second configuration data using the second wireless auxiliary communication; determining whether the medical accessory and the second medical accessory are of a same type based on the configuration data and the second configuration data; and, if the medical accessory and the second medical accessory are of the same type: inhibiting data communication using the wireless operating communication with the second medical accessory and closing the second wireless auxiliary communication.

In a 9th aspect according to anyone of the preceding aspects, after the wireless operating communication has been established, the method further comprises the steps of comparing an idle time interval indicative of a time interval since the last data communication between the fluid processing medical device and the medical accessory using the wireless operating communication with a pre-defined maximum idle time interval; and closing the wireless operating communication if the idle time interval is greater than the pre-defined maximum idle time interval.

In a 10th aspect according to the preceding aspect, the method further comprises the step of performing an alarm procedure if the idle time interval is greater than the pre-defined maximum idle time interval.

In a 11th aspect according to anyone of the preceding aspects, the step of establishing the wireless auxiliary communication is preceded by a step of bringing a data storage unit of the medical accessory into a close proximity of a data acquisition unit of the fluid processing medical device in order to initiate the establishing of the wireless auxiliary communication, the close proximity being equal to or shorter than the maximum operating distance of the wireless auxiliary communication, the medical accessory and the fluid processing medical device establishing said wireless auxiliary communication when the data storage unit is in the close proximity of the data acquisition unit.

In a 12th aspect according to the preceding aspect, the data storage unit of the medical accessory comprises an optical bar-code or an optical matrix code (QR-code), and the data acquisition unit of the fluid processing medical device comprises an optical reader, in particular a bar-code reader or a matrix code reader configured to read the optical bar code or the optical matrix code.

In a 13th aspect according to the preceding aspect 11, the data storage unit of the medical accessory comprises a near field communication (NFC/RFID) unit, the near field communication unit optionally comprising a near field communication transmitter and receiver, and the data acquisition unit of the fluid processing medical device comprises a near field communication reader configured to read data from the near field communication transmitter and receiver.

In a 14th aspect according to anyone of the preceding aspects, the configuration data comprise status data indicative of an operating configuration of the medical accessory, and the step of establishing the wireless operating communication further comprises determining, based on the status data, whether the medical accessory is in a status configured for operation with the fluid processing medical device.

In a 15th aspect according to anyone of the preceding aspects, the wireless operating communication is configured to operate at a maximum bandwidth higher than a maximum bandwidth of the wireless auxiliary communication, and/or on a wireless frequency range different from a wireless frequency of the wireless auxiliary communication, and/or according to a wireless network protocol different from a wireless network protocol of the wireless auxiliary communication.

In a 16th aspect according to the preceding aspect, the wireless frequency range of the wireless auxiliary communication is:

a visible or near infra-red optical frequency range, in particular from about 4*1014 Hz to about 9.35*1014 Hz, or a microwave frequency range, in particular from about 13.553 MHz to about 13.567 MHz, and/or the wireless frequency range of the operating communication is:

from about 868 MHz to about 868.6 MHz;
from about 902 MHz to about 928 MHz;
from about 2.4 GHz to about 2,485 GHz, or
from about 5,150 GHz to about 5,850 GHz.

In a 17th aspect according to anyone of the preceding aspects, the wireless auxiliary communication is based on one of:

near field communication (NFC/RFID), and
optical recognition, in particular, optical bar-code recognition and optical matrix code (QR-code) recognition.

In a 18th aspect according to anyone of the preceding aspects, the wireless operating communication is based on one of:

wireless local area network, particularly according to standard WLAN IEEE 802.11, and
Bluetooth, particularly according to standard IEEE 802.15.1 and/or IEEE 802.15.4.

In a 19th aspect according to anyone of the preceding aspects, the method further comprising the step of closing the wireless auxiliary communication after the configuration data has been transferred.

In a 20th aspect according to anyone of the preceding aspects, establishing the wireless auxiliary connection comprises detecting the presence of the data storage unit of the medical accessory within an initial distance to the data acquisition unit of the fluid processing medical device, the initial distance being equal to or shorter than the maximum operating distance of the wireless auxiliary communication.

In a 21st aspect according to the preceding aspect, detecting the presence of the data storage unit of the medical accessory within the initial distance comprises scanning an optical pattern visibly attached to the medical accessory; and decoding the configuration data from the optical pattern.

In a 22nd aspect according to the preceding aspect 20, detecting the presence of the data storage unit of the medical accessory within the initial distance comprises sending an electromagnetic signal from the data acquisition unit of the fluid processing medical device to the data storage unit of the medical accessory to initiate the wireless auxiliary communication, the electromagnetic signal optionally being sent in order to supply energy to a transponder or transceiver comprised in the data storage unit of the medical accessory; and receiving the configuration data in response to the electromagnetic signal and by means of the wireless auxiliary communication.

In a 23rd aspect according to anyone of the preceding aspects, the wireless auxiliary communication is configured for the transfer of the configuration data from the medical accessory to the fluid processing medical device.

In a 24th aspect according to anyone of the preceding aspects 1 to 22, the wireless auxiliary communication is configured for bi-directional data transfer between the medical accessory and the fluid processing medical device.

In a 25th aspect according to anyone of the preceding aspects, the method comprises connecting the medical accessory to a patient; generating at the medical accessory treatment data based on one or more physical characteristics of the patient, the one or more physical characteristics being measured using the medical accessory; and transferring the treatment data to the fluid processing medical device using the wireless operating communication.

In a 26th aspect according to the preceding aspect, the treatment data comprise one or more values of the physical characteristics, the physical characteristics being selected from a group consisting of: patient's blood pressure, patient's weight, patient's temperature, patient's heart rate, patient's oxygen saturation in blood, blood leakage of patient's blood in correspondence of a vascular access.

In a 27th aspect according to anyone of the preceding aspects, the medical accessory is connected to the patient after the configuration data has been transferred.

In a 28th aspect depending on any of the previous aspects 1 to 27, the fluid processing medical device is a blood treatment device, in particular an extracorporeal blood treatment device.

In a 29th aspect depending on any of the previous aspects 1 to 27, the fluid processing medical device is an infusion pump, particularly including a main body portion, a display contained on the main body portion for displaying user interface information; at least one pump module secured to the main body portion and adapted to receive a tube, the pump module having means for applying pumping action to the tube; and a pump control unit associated to the main body portion for generating user interface information on the display areas.

A 30th independent aspect of the invention concerns a fluid processing medical device, comprising a main body portion, a display contained on the main body portion for displaying user interface information; at least one pump module secured to the main body portion and adapted to receive a tube, the pump module having means for applying pumping action to the tube; and a device control unit associated to the main body portion for generating user interface information on the display areas, the device control unit of the fluid processing medical device being programmed to perform the steps of establishing a wireless auxiliary communication between the fluid processing medical device and a medical accessory; transferring configuration data using the wireless auxiliary communication; and establishing a wireless operating communication between the fluid processing medical device and the medical accessory based on the configuration data, wherein a maximum operating distance of the wireless auxiliary communication is shorter than a maximum operating distance of the wireless operating communication.

A 31st independent aspect of the invention concerns an extracorporeal blood treatment device, comprising a blood treatment unit having a blood chamber and a fluid chamber which are separated from one another by a semipermeable membrane; an extracorporeal blood circuit having an arterial line for blood removal from an individual and a venous line for blood return to the individual, the arterial line and the venous line being connected to an inlet and, respectively, to an outlet of the blood chamber; a blood moving device configured for moving the blood along the extracorporeal circuit; a fluid circuit having at least a discharge line connected to an outlet of the fluid chamber; an ultrafiltration device configured for ultrafiltering plasmatic liquid from the blood chamber to the fluid chamber across the semipermeable membrane; a device control unit of the blood treatment device, the device control unit being programmed to perform the steps of establishing a wireless auxiliary communication between the blood treatment device and a medical accessory; transferring configuration data using the wireless auxiliary communication; and establishing a wireless operating communication between the blood treatment device and the medical accessory based on the configuration data, wherein a maximum operating distance of the wireless auxiliary communication is shorter than a maximum operating distance of the wireless operating communication.

A 32nd independent aspect of the invention concerns an infusion pump comprising a main body portion, a display contained on the main body portion for displaying user interface information; at least one pump module secured to the main body portion and adapted to receive a tube, the pump module having means for applying pumping action to the tube; and a device control unit associated to the main body portion for generating user interface information on the display areas, the device control unit of the fluid processing medical device being programmed to perform the steps of establishing a wireless auxiliary communication between the fluid processing medical device and a medical accessory; transferring configuration data using the wireless auxiliary communication; and establishing a wireless operating communication between the fluid processing medical device and the medical accessory based on the configuration data, wherein a maximum operating distance of the wireless auxiliary communication is shorter than a maximum operating distance of the wireless operating communication.

In a 33rd aspect according to anyone the preceding aspects 30 to 32, the maximum operating distance of the wireless auxiliary communication is less than 2 m, preferably the maximum operating distance of the wireless auxiliary communication is equal to or less than 20 cm, more preferably the maximum operating distance of the wireless auxiliary communication is equal to or less than 10 cm.

In a 34th aspect according to anyone of the preceding aspects 30 to 33, the maximum operating distance of the wireless operating communication is equal to or greater than 2 m, preferably the maximum operating distance of the wireless operating communication is equal to or greater than 10 m.

In a 35th aspect according to anyone of the preceding aspects 30 to 34, the step of establishing the wireless operating communication further comprises the steps of determining, based on the configuration data, communication data of the medical accessory, the communication data of the medical accessory being configured for operation with the wireless operating communication, the communication data further being indicative of a communication configuration of the medical accessory;
initiating, based on the communication data, a data communication between the fluid processing medical device or blood treatment device or infusion pump and the medical accessory by means of the wireless operating communication.

In a 36th aspect according to anyone of the preceding aspects 30 to 35, the configuration data comprise type data indicative of a plurality of properties of the medical accessory.

In a 37th aspect according to anyone of the preceding aspects 30 to 35, the step of establishing the wireless operating communication further comprises determining, based on the type data, whether the medical accessory is of a type suitable for operation with the fluid processing medical device or blood treatment device or infusion pump; and closing both the wireless auxiliary communication and the wireless operating communication, if the medical accessory is not of a type suitable for operation with the fluid processing medical device or blood treatment device or infusion pump.

In a 38th aspect according to anyone of the preceding aspects 30 to 37, the plurality of properties of the medical accessory that the type data are indicative of, comprise one or more of hardware data indicative of a hardware configuration of the medical accessory; software data indicative of a software configuration of the medical accessory; and firmware data indicative of a firmware configuration of the medical accessory, and the step of determining whether the medical accessory is of a type suitable for operation with the fluid processing medical device or blood treatment device or infusion pump is based on one or more of the hardware data, the software data, and the firmware data.

In a 39$^{th}$ aspect according to anyone of the preceding aspects 30 to 38, after the wireless operating communication has been established, the method further comprises the steps of establishing a second wireless auxiliary communication between the fluid processing medical device or blood treatment device or infusion pump and a second medical accessory; transferring second configuration data using the second wireless auxiliary communication; determining whether the medical accessory and the second medical accessory are of a same type based on the configuration data and the second configuration data; and inhibiting data communication using the wireless operating communication with the second medical accessory if the medical accessory and the second medical accessory are of the same type.

In a 40$^{th}$ aspect according to anyone of the preceding aspects 30 to 39, after the wireless operating communication has been established, the method further comprises the steps of comparing an idle time interval indicative of a time interval since the last data communication between the fluid processing medical device or blood treatment device or infusion pump and the medical accessory using the wireless operating communication with a pre-defined maximum idle time interval; and closing the wireless communication if the idle time interval is greater than the pre-defined maximum idle time interval.

In a 41$^{st}$ aspect according to the preceding aspect, the fluid processing medical device or blood treatment device or infusion pump further comprises the step of performing an alarm procedure if the idle time interval is greater than the pre-defined maximum idle time interval.

In a 42$^{nd}$ aspect according to anyone of the preceding aspects 30 to 41, the step of establishing the wireless auxiliary communication is preceded by a step of bringing a data storage unit of the medical accessory into a close proximity of a data acquisition unit of the fluid processing medical device or blood treatment device or infusion pump in order to initiate the establishing of the wireless auxiliary communication, the close proximity being equal to or shorter than the maximum operating distance of the wireless auxiliary communication, the medical accessory and the fluid processing medical device or blood treatment device or infusion pump establishing said wireless auxiliary communication when the data storage unit is in the close proximity of the data acquisition unit.

In a 43$^{rd}$ aspect according to the preceding aspect, the data storage unit of the medical accessory comprises an optical bar-code or an optical matrix code (QR-code), and the data acquisition unit of the fluid processing medical device or blood treatment device or infusion pump comprises an optical reader, in particular a bar-code reader or a matrix code reader configured to read the optical bar code or the optical matrix code.

In a 44$^{th}$ aspect according to the preceding aspect 42, the data storage unit of the medical accessory comprises a near field communication (NFC/RFID) unit, the near field communication unit optionally comprising a near field communication transmitter and receiver, and the data acquisition unit of the fluid processing medical device or blood treatment device or infusion pump comprises a near field communication reader configured to read data from the near field communication transmitter and receiver.

In a 45$^{th}$ aspect according to anyone of the preceding aspects 30 to 42, the configuration data comprise status data indicative of an operating configuration of the medical accessory, and the step of establishing the wireless operating communication further comprises determining, based on the status data, whether the medical accessory is in a status configured for operation with the fluid processing medical device or blood treatment device or infusion pump.

In a 46$^{th}$ aspect according to anyone of the preceding aspects 30 to 45, the wireless operating communication is configured to operate at a maximum bandwidth higher than a maximum bandwidth of the wireless auxiliary communication, and/or on a wireless frequency range different from a wireless frequency of the wireless auxiliary communication, and/or according to a wireless network protocol different from a wireless network protocol of the wireless auxiliary communication.

In a 47$^{th}$ aspect according to anyone of the preceding aspects 30 to 46, the wireless frequency range of the wireless auxiliary communication is 13.553 MHz to 13.567 MHz, and/or the wireless frequency range of the operating communication is one of:
about 868 MHz to about 868.6 MHz
about 902 MHz to about 928 MHz
about 2.4 GHz to about 2,485 GHz, and
about 5,150 GHz to about 5,850 GHz.

In a 48$^{th}$ aspect according to anyone of the preceding aspects 30 to 47, the wireless auxiliary communication is based on one of near field communication (NFC/RFID), and optical recognition, in particular, optical bar-code recognition and optical matrix code (QR-code) recognition.

In a 49$^{th}$ aspect according to anyone of the preceding aspects 30 to 48, the wireless operating communication is based on one of wireless local area network, in particular according to standard WLAN IEEE 802.11, an Bluetooth, in particular according to standard IEEE 802.15.1 and/or IEEE 802.15.4.

In a 50$^{th}$ aspect according to anyone of the preceding aspects 30 to 49, the fluid processing medical device or blood treatment device or infusion pump device further comprises the step of closing the wireless auxiliary communication after the configuration data has been transferred.

In a 51$^{st}$ aspect according to anyone of the preceding aspects 30 to 50, establishing the wireless auxiliary connection comprises:
detecting the presence of the medical accessory within an initial distance to the fluid processing medical device or blood treatment device or infusion pump, the initial distance being equal to or shorter than the maximum operating distance of the wireless auxiliary communication.

In a 52$^{nd}$ aspect according to anyone of the preceding aspects 30 to 51, detecting the presence of the medical accessory within the initial distance comprises scanning an optical pattern visibly attached to the medical accessory; and decoding the configuration data from the optical pattern.

In a 53$^{rd}$ aspect according to the preceding aspect, detecting the presence of the medical accessory within the initial distance comprises sending an electromagnetic signal to the medical accessory to initiate the wireless auxiliary communication, the electromagnetic signal optionally being sent in order to supply energy to a transponder comprised in the medical accessory; and receiving the configuration data in response to the electromagnetic signal and by means of the wireless auxiliary communication.

In a 54th aspect according to anyone of the preceding aspects 30 to 53, the wireless auxiliary communication is configured for the transfer of the configuration data from the medical accessory to the fluid processing medical device or blood treatment device or infusion pump.

In a 55th aspect according to anyone of the preceding aspects 30 to 54, the wireless auxiliary communication is configured for bi-directional data communication between the medical accessory and the fluid processing medical device or blood treatment device or infusion pump.

In a 56th aspect according to anyone of the preceding aspects 30 to 55, the blood treatment device further comprises an infusion circuit having at least a first supply line of an infusion fluid connected to the extracorporeal blood circuit; and an infusion fluid supply device configured to supply the infusion fluid along the first supply line.

In a 57th aspect according to anyone of the preceding aspects 30 to 55, the fluid processing medical device or blood treatment device or infusion pump further comprises one or more of an optical reader, in particular a bar-code reader or a matrix code reader, an NFC device configured for communication with an NFC device associated with the medical accessory.

In a 58th aspect according to anyone of the preceding aspects 30 to 55, the medical accessory comprises one of an optical code comprising the configuration data, in particular a bar-code or a matrix code, and a second NFC device configured for communication with the NFC device associated with the fluid processing medical device or blood treatment device or infusion pump, optionally the second NFC device being a passive NFC tag configured for operating power from an external source.

In a 59th aspect according to anyone of the preceding aspects 30 to 58, the medical accessory further comprises a sensor configured to measure one or more physical characteristics of a patient, the physical characteristics being selected from a group consisting of: patient's blood pressure, patient's weight, patient's temperature, patient's heart rate, patient's oxygen saturation in blood, blood leakage of patient's blood in correspondence of a vascular.

In a 60th aspect according to the preceding aspect, the medical accessory further comprises a controller operatively connected to the sensor and configured to generate treatment data based on the one or more physical characteristics.

In a 61st aspect according to anyone of the preceding aspects 59 to 60, the medical accessory comprises an accessory control unit configured for comparing the one or more measured physical characteristics to one or more corresponding pre-defined control ranges; and performing an alarm procedure based on the comparison, if a value of any one of the one or more measured physical characteristics is not within the corresponding pre-defined control range; optionally performing the alarm procedure comprises: sending an alarm signal to the fluid processing medical device or blood treatment device or infusion pump using the wireless operating communication, or generating an alarm signal locally within the medical accessory.

In a 62nd aspect according to anyone of the preceding aspects 59 to 61, the accessory control unit is configured for transferring the treatment data to the fluid processing medical device or blood treatment device or infusion pump using the wireless operating communication; optionally the medical accessory is configured for preventing transfer of the treatment data using the wireless auxiliary communication.

In a 63rd aspect according to anyone of the preceding aspects 59 to 61, the accessory control unit is configured for inhibiting data communication with a second fluid processing medical device or a second blood treatment device or a second infusion pump over the wireless operating communication until the wireless operating communication with the fluid processing medical device or blood treatment device or infusion pump is closed.

In a 64th aspect according to anyone of the preceding aspects 30 to 59, the medical accessory is configured to be connected to any one of a number of a plurality of fluid processing medical devices or blood treatment devices or infusion pumps.

In a 65th aspect according to anyone of the preceding aspects 30 to 64, the medical accessory is configured to be not connectable to any one of a number of a plurality of medical accessories.

In a 66th aspect according to anyone of the preceding aspects 30 to 65, the medical accessory has a transmitter configured for transmitting wireless signals over a wireless operating communication, optionally the medical accessory further has a receiver configured for receiving wireless signals over a wireless operating communication.

In a 67th aspect according to anyone of the preceding aspects 30 to 66, the medical accessory is selected from a group comprising a pressure cuff, a scale, an oxipulsimeter, a temperature sensor, a wireless reader, in particular an optical reader, an ECG monitor, a blood leak detector.

In a 68th aspect according to anyone of the preceding aspects 30 to 67, the fluid processing medical device or blood treatment device or infusion pump and the medical accessory are not physically connected.

In a 69th aspect according to anyone of the preceding aspects 30 to 68, the medical accessory is configured for transferring treatment data.

In a 70th aspect according to anyone of the preceding aspects 30 to 69, the fluid processing medical device or blood treatment device or infusion pump has a receiver configured for receiving wireless signals over a wireless operating communication, optionally the fluid processing medical device or blood treatment device or infusion pump further has a transmitter configured for transmitting wireless signals over a wireless operating communication.

In a 71st aspect according to anyone of the preceding aspects 30 to 70, the blood treatment device is one of a hemofiltration device, a hemodiafiltration device, an ultrafiltration device, and a plasmapheresis device.

In a 72nd aspect according to anyone of the preceding aspects 30 to 71, the medical accessory is a wireless reader configured to read data on an information carrier of a component installed or to be installed on the fluid processing medical device or blood treatment device or infusion pump.

In a 73rd aspect according to the preceding aspect, the information carrier is one selected in the group comprising: a surface of the component, a packaging of the component, a card associated with the component.

In a 74th aspect according to the preceding aspect, the information comprises one or more selected in the group including:
Identity of the component, Identity of a series of identical components, Expiration date of the component, Manufacturer, One or more commands for programming the apparatus to execute a procedure on said fluid, Data concerning a patient.

In a 75th aspect according to anyone of the preceding aspects 72 to 74, the wireless reader comprises an optical reader or a radio-frequency reader adapted to detect said information when the component and the reading portion are approached one another at a distance less then 30 cm.

In a 76th aspect according to anyone of the preceding aspects 72 to 75, the extracorporeal blood treatment device further comprises a support structure supporting at least the ultrafiltration device and the blood moving device, a plurality of replaceable components of different categories engaged to the support structure in correspondence of respective operating areas, each component of a same category having respective mechanical connection to a corresponding operating area on the support structure, different from that of components of other categories, said support structure includes a plurality of different types of engaging means, each type of engaging means being designed for mechanically engaging, in a respective operating area, a component of one corresponding category only, at least a user interface enabling setting of a plurality of parameters pertinent to operation of said extracorporeal blood treatment device or pertinent to a process to be performed by said extracorporeal blood treatment device, the user interface including at least a screen, the wireless reader having a reading portion for reading information concerning the components, the reading portion being spaced from said operating areas and accessible for reading the information irrespective of the components being engaged or not to the support structure, the device control unit of the blood treatment device controls operation of said blood treatment device and is responsive to actions by a user on said user interface, said device control unit also communicating with the wireless reader and being programmed for receiving and storing at least said information concerning the components every time the reader reads information concerning a new component installed or to be installed on the apparatus.

A 77th independent aspect concerns a medical system, comprising a plurality of the fluid processing medical devices or blood treatment devices or infusion pumps according to any one of aspects 30 to 76 and a plurality of medical accessories.

In a 78th aspect according to anyone of the previous aspects, the configuration data comprise one or more of identification data comprising a unique identifier associated to the medical apparatus, and wherein the step of establishing the wireless communication between the medical accessory and the medical apparatus is based on the unique identifier; type data indicative of one or more properties of the medical apparatus, optionally wherein the one or more properties of the medical accessory that the type data are indicative of, comprise one or more of hardware data indicative of a hardware configuration of the medical accessory; software data indicative of a software configuration of the medical accessory; and firmware data indicative of a firmware configuration of the medical accessory, and the step of establishing the wireless communication between the medical accessory and the medical apparatus comprises determining whether the medical apparatus is of a type suitable for operation with the medical accessory based on one or more of the hardware data, the software data, and the firmware data; status data indicative of an operating configuration of the medical apparatus, and wherein the step of establishing the wireless communication between the medical accessory and the medical apparatus comprises determining, based on the status data, whether the medical apparatus is in a status configured for operation with the medical component.

DESCRIPTION OF THE DRAWINGS

The following drawings relating to aspects of the invention are provided by way of non-limiting example.

DETAILED DESCRIPTION

Figure 1:
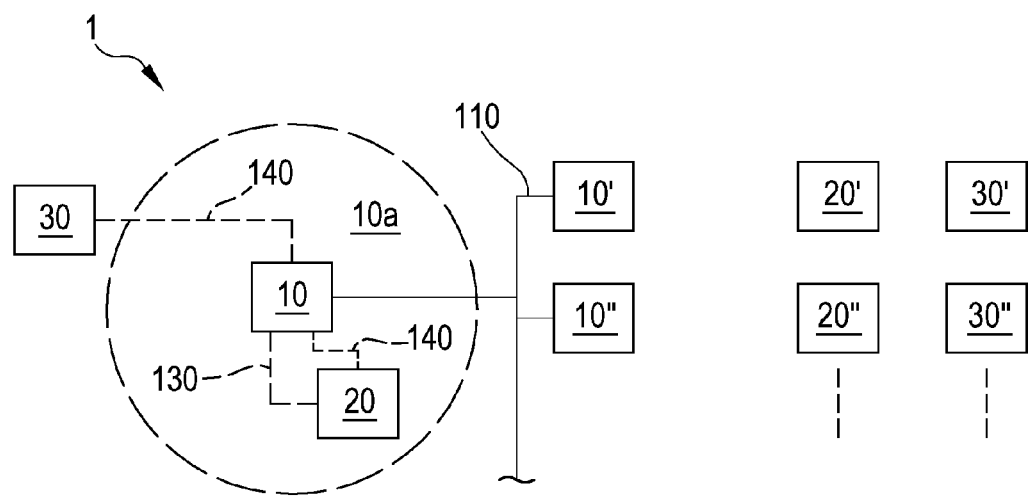
FIG. 1 shows an example network infrastructure, in which the process for establishing a wireless operating configuration in accordance with the invention can be employed.

With reference to the following description, a wireless auxiliary communication provides data communication for the purpose of transferring configuration data necessary for establishing a wireless operating communication. The auxiliary communication can be a low range and/or low bandwidth communication, for example requiring close proximity of the communicating entities or units. In particular, the auxiliary communication can be a unidirectional communication. Preferably, the wireless auxiliary communication is a bi-directional communication.

In some examples, the wireless auxiliary communication is realized using optical means, in which an optical scanner detects an optical element present in the vicinity of the scanner. For example, the medical accessory can have an optical pattern (e.g. bar-code or QR-code) affixed thereto and configured for detection by an optical scanner comprised in the fluid processing medical device or blood treatment device or infusion pump.

In the detailed description reference is made to a blood treatment device mainly; however, all described technical features and characteristics are equally applicable in general to a fluid processing medical device such as a blood treatment device or an infusion pump. The fluid processing device may include or be associated to a monitoring apparatus. The monitoring apparatus may be configured to monitor data acquired by the fluid processing apparatus and/or by the medical accessory.

Upon bringing the medical accessory into the proximity of the blood treatment device (more precisely, upon bringing the data storage unit of the medical accessory into the proximity of the data acquisition unit of the blood treatment device), so that the optical scanner of the blood treatment device can detect and scan the optical pattern, the data encoded in the optical pattern can be scanned and decoded by the blood treatment device. In this example, the data storage unit of the medical accessory is the optical pattern having information encoded therein, and the data acquisition unit of the blood treatment device is the optical scanner configured to scan the optical pattern and, optionally, to decode it. For a detection to be possible, the distance between the medical accessory and the blood treatment device (more precisely, between the optical pattern and the optical scanner, i.e. between the data storage unit and the data acquisition unit) is typically 2 m or less. In some examples, the distance can be 1 m or less, or even 50 cm or less. In general, the optical scanner and the optical pattern can be configured to facilitate detection and scanning at any desired distance within the optical limitations for optical scanning equipment, for example by adapting the size of the optical pattern and/or providing the optical scanner with one or more suitable light sources, optical lenses, or other optical components required for scanning at the desired distance. For example, a larger optical pattern and/or a longer focal length can facilitate detection from a farther distance.

In one example, a QR-code is used. The data capacity of a QR-code depends on its version number and the level of error correction. The data capacity ranges from about 10 (version 1) to about 4.000 (version 40) alphanumeric characters. A QR-code has error correction capability to restore data if the code cannot be scanned entirely correctly, for example due to optical effects or wear of the original pattern. Four error correction levels L, M, Q, and H are available, offering error correction from about 7% (level "L") to about 30% (level "H") of total code words (one code word being equal to 8 bits of information). The maximum distance at which a QR-code can be reliably read depends on technical factors (e.g. optical properties of scanner, size and version of the QR-code pattern, etc.) and external factors (e.g. lighting). Typically, the maximum reading distance is about 10 times the size of the QR-code (e.g. for version 2 QR-codes). In one example, if the (version 2) QR-code has a size of 25 mm×25 mm, the maximum reading distance is about 25 cm. The desired maximum reading distance can, thus, easily be pre-determined by reducing or enlarging the size of the QR-code to be read.

In other examples, the wireless auxiliary communication is realized using electromagnetic communication means, in which a transmitter sends out an electromagnetic signal that can be received by a receiver. For example, the medical accessory can have a near filed communication (NFC) unit (e.g. RFID code or suitable transmitter/receiver) associated thereto and configured for communication with a corresponding NFC unit associated to the blood treatment device. Upon bringing the medical accessory into the proximity of the blood treatment device (more precisely, upon bringing the data storage unit of the medical accessory into the proximity of the data acquisition unit of the blood treatment device), so that the NFC unit of the blood treatment device can detect and receive signals from the NFC unit of the medical accessory, the data encoded in the transferred signal can be received and decoded by the blood treatment device. In this example, the data storage unit is the NFC unit (e.g. RFID tag; active or passive) of the medical accessory, and the data acquisition unit is the NFC unit (e.g. RFID reader) of the blood treatment device. For a detection to be possible, the distance between the data storage unit of the medical accessory and the data acquisition unit of the blood treatment device (i.e., between the two NFC units and/or their components, e.g. antennae, etc.) is typically 2 m or less. In some examples, the distance can be 20 cm or less, or even 10 cm or less. In general, the NFC units can be configured to facilitate detection and scanning at any desired distance within the designed operating range of NFC units.

With reference to the following description, a wireless operating communication provides data communication for the purpose of transferring bulk data (e.g. medical data, treatment data, etc.) necessary for data communication between the medical accessory and the blood treatment device. Typically, the medical accessory measures and encodes patient parameter values for transmission to the blood treatment device, maintaining data communication with the blood treatment device for longer periods of time (e.g. 1 h or more). Transferred bulk data can include, but is not limited to, for example: the blood pressure of a patient, the weight of a patient, the body temperature of a patient, the heart rate of a patient, the oxygen saturation in blood of a patient, the leakage of a patient's blood in correspondence of a vascular access, and/or values of other parameters indicative of physical characteristics of a patient. The operating communication can be a medium to long range and/or medium to high bandwidth communication. In particular, the operating communication can be a bi-directional communication. The medical accessory can store bulk data during time periods in which the wireless operating communication is not available. For example, the medical accessory may generate bulk data (e.g. heart rate, respiratory rate, $SPO_2$, skin temperature, sweat, patient activity, hydration, cutaneous blood perfusion/volume, glucose) over extended periods of time irrespective of an ongoing treatment. In particular, the medical accessory may generate bulk data between treatment sessions when the patient is typically not under medical care and/or is not present at a medical facility. The medical accessory stores the bulk data generated in order to be transferred, for example to the fluid processing device or to the monitoring apparatus such that the bulk data can be checked for consistency, that the patient's parameters may be monitored during treatment based on a histogram of one or more of the same parameters that has been generated based on the bulk data, and/or that the long term development of one or more of the bulk data can be taken into account for the treatment. The bulk data may be evaluated before, during, and/or after the treatment session. In particular, the bulk data can be evaluated during the treatment session, thereby allowing for real-time monitoring of the patient's parameters during the treatment. In rare examples and for very specific applications, the wireless operating communication can be a unidirectional communication.

With reference to the appended drawings, FIG. 1 shows an example network infrastructure, in which the process for establishing a wireless operating configuration in accordance with the invention can be employed. A system 1 generally comprises one or more blood treatment devices 10, 10', 10", etc. and one or more medical accessories 20, 20', 20", etc. The blood treatment devices 10, 10', 10" can be in data communication using a wired network 110. Alternatively (not illustrated), blood treatment devices 10, 10', 10" can be in data communication using a wireless network 120.

Proximity to blood treatment device 10 is illustrated by dashed line 10a, wherein an accessory 20 within dashed line 10a is regarded as being in proximity to blood treatment device 10. It is noted that this concept of proximity is purely an abstract concept, very much depending upon the properties of the wireless auxiliary communication, which defines the concept of proximity due to its technical limitations. As described above, the proximity of the data storage unit of the medical accessory to the data acquisition unit of the blood treatment device is relevant here. It might, therefore, be (also) required, to orient or align the accessory with the device in a manner that brings the data storage unit of the accessory into the required proximity to the data acquisition unit of the device. In one example, this can require holding the accessory with the data storage unit (e.g. an optical code or RFID tag) in front of, close to, and generally facing towards the data acquisition unit (e.g. optical reader or RFID reader) of the blood treatment device.

For example, if the wireless auxiliary communication is based on optical pattern scanning (see above), then the proximity to a blood treatment device 10 could be defined as a portion of space relative to blood treatment device 10, in which an optical scanner (i.e. the data acquisition unit) of device 10 can detect and scan an optical pattern (i.e. the data storage unit) present on an accessory 20. In this example, the portion of space can have a frustoconical shape situated in front of the optical scanner.

In another example, if the wireless auxiliary communication is based on NFC (see above), then the proximity to a blood treatment device 10 could be defined as a portion of space relative to blood treatment device 10, in which an NFC unit (i.e. the data acquisition unit) of device 10 can detect the presence of an NFC unit (i.e. the data storage unit) of accessory 20 and receive an electromagnetic signal transmitted therefrom. In this example, the portion of space can have a substantially spherical shape situated around the NFC unit of device 10.

In FIG. 1, the proximity to blood treatment device 10 is illustrated by dashed line 10a denoting a spherical portion of space around device 10. As shown, establishing a wireless auxiliary communication between device 10 and accessory 20 would be possible, since accessory 20 is in proximity of device 10. Accessories 20' and 20" however, would not be able to establish a wireless auxiliary communication with device 10, because accessories 20' and 20" are located too far away from device 10, thereby being outside the maximum operating distance of the wireless auxiliary communication. Establishing a wireless operating communication between any of accessories 20' or 20" and device 10 would, therefore, not be possible using the method described herein—unless the accessories are brought into proximity to device 10.

As shown, an auxiliary data communication 130 has been established between accessory 20 and device 10, and a wireless operating communication 140 has also been established between accessory 20 and device 10. The wireless auxiliary communication between accessory 20 and device 10 can subsequently be closed, a state not illustrated in FIG. 1. It is further noted that generally the accessories 20, 20', 20", 30, 30', 30", etc. are configured to connect only to a single device 10, 10', 10" at the same time. However, depending upon the properties of devices, accessories, treatments, applications, etc., it can be desirable to have exceptions to this rule. Similarly, generally the devices 10, 10', 10", etc. are configured to be able to connect to one or more accessories 20, 20', 20", 30, 30', 30", etc. at the same time. However, depending upon the properties of devices, accessories, treatments, applications, etc., it can be desirable to have exceptions to this rule (e.g. a device being configured to connect only to a single accessory at a time).

Further, a second accessory 30 of a different type than accessory 20 is also in a wireless operating communication with device 10, wherein the wireless auxiliary communication between accessory 30 and device 10 has already been closed as it is no longer required. It is noted that it can be desirable to maintain a wireless operating communication between an accessory 20, 20', 20", 30, 30', 30" etc. even if the accessory leaves the proximity of device 10. In some examples (e.g., when an optical pattern and optical scanner are used), it might be required to remove the accessory (i.e. the data storage unit of the accessory) from the proximity of the device (i.e. the data acquisition unit of the device) when the wireless operating communication has been established, because the medical accessory has to be fitted to the patient in order to measure, encode, and transmit the required treatment data. For example, a medical accessory measuring the blood pressure of a patient has to be attached to a limb of the patient. It is understood that, upon establishing the wireless operating communication between the blood treatment device, which the patient is connected to, and the medical accessory, it is no longer required for the data storage unit of the medical accessory to remain in close proximity to the data acquisition unit of the blood treatment device, so that the medical accessory can be fitted to the patient and the patient can comfortably rest upon a proper support during the treatment performed by the blood treatment device.

Depending upon the specific properties of the device, accessory, treatment, application, etc., it can alternatively be desired to close the wireless operating communication as soon as the accessory is no longer in proximity to the device (additionally or alternatively, an alarm procedure can be performed). FIG. 1 illustrates accessories 20 and 30 each being in a respective wireless operating communication with device 10. Additional accessories 30', 30", etc. and the handling thereof essentially corresponds to that of accessories 20, 20', 20", etc. as described above. As shown in FIG. 1, accessories 20', 20", etc. are illustrated as not being in a wireless operating communication with device 10. For example, medical accessory 20' may be associated to a patient who is presently not undergoing treatment, but is carrying the medical accessory outside of the medical facility in order to acquire bulk data (see above) indicative of one or more patient parameters. Upon return to the medical facility (e.g. for a treatment session), medical accessory 20' may establish a wireless operating communication as described above in order to provide the fluid processing device and/or a monitoring apparatus with the acquired bulk data. Providing the bulk data includes providing previously acquired data as a block of data transferred to the fluid processing device and/or monitoring apparatus. Providing the bulk data further includes continuously providing data currently acquired by the medical accessory.

Figure 2:
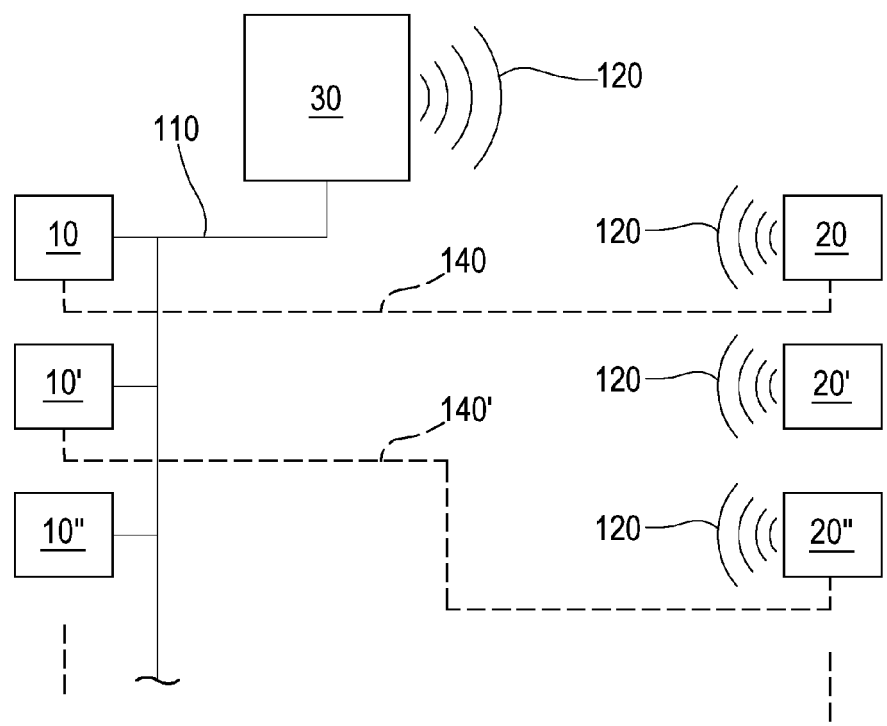
FIG. 2 shows another exemplary network infrastructure, in which the process for establishing a wireless operating configuration in accordance with the invention can be employed.

FIG. 2 shows another exemplary network infrastructure, in which the process for establishing a wireless operating configuration in accordance with the invention can be employed. FIG. 2 does not show the proximity of any device 10, 10', 10", etc. but focuses on the manner a wireless operating communication can be realized. As illustrated in FIG. 2, a number of blood treatment devices 10, 10', 10", etc. are associated to a wired network. Further, a wireless access point 30 or similar apparatus provides a wireless network connection 120, substantially spanning an overall network across the wired and wireless networks, effectively connecting all devices 10, 10', 10" and accessories 20, 20', 20" to one another. As illustrated, a wireless auxiliary communication (already closed and, therefore, not shown) between accessory 20 and device 10 has facilitated establishing a wireless operating connection 140 between device 10 and accessory 20. Device 10 and accessory 20 can communicate vie the wireless operating communication 140, which is realized by means of wireless network 120 (i.e. between accessory 20 and access point 30) and further by means of wired network 110 (i.e. between access point 30 and device 10). The physical network connection is transparent for the wireless operating communication 140. In a similar manner, a wireless operating communication 140' has been established between accessory 20" and device 10'.

Figure 3:
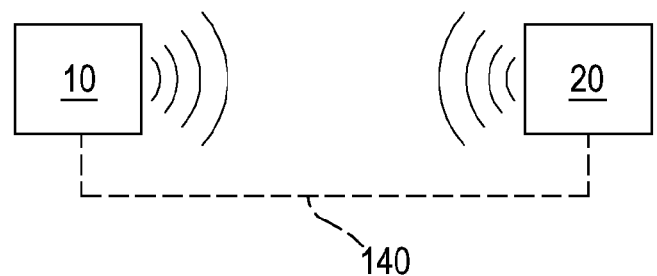
FIG. 3 shows an example of a direct communication between a device 10 and an accessory 20, in which the process for establishing a wireless operating configuration in accordance with the invention can be employed.

FIG. 3 shows an example of a direct communication between a device 10 and an accessory 20, in which the process for establishing a wireless operating configuration in accordance with the invention can be employed. With reference to FIGS. 2 and 3, it is noted that the presence of a network infrastructure 110, 120 as shown in FIG. 3 is not necessarily required. As shown in FIG. 3, a wireless operating communication 140 between accessory 20 and device 10 can also be established directly, namely without any intermediate network infrastructure, wherein device 10 and accessory 20 communicate directly with one another. In one example, the direct communication between device 10 and accessory 20 is realized using an ad-hoc WLAN connection.

A wireless ad-hoc network is a decentralized type of wireless network. The network is referred to as "ad-hoc" because it does not rely on an intermediate network infrastructure (e.g. including routers or access points in managed (so-called "infrastructure") wireless networks). Instead, each node participates in routing by forwarding data for other nodes, so the determination of which nodes forward data is made dynamically on the basis of network connectivity. In the example shown in FIG. 3, two network devices are in data communication using an ad-hoc WLAN connection created between the two network devices, i.e. device 10 and accessory 20. The wireless operating communication is independent from the manner in which the data communication between two network devices is realized, as long as the concrete realization facilitates establishing the wireless operating communication.

Figure 4:
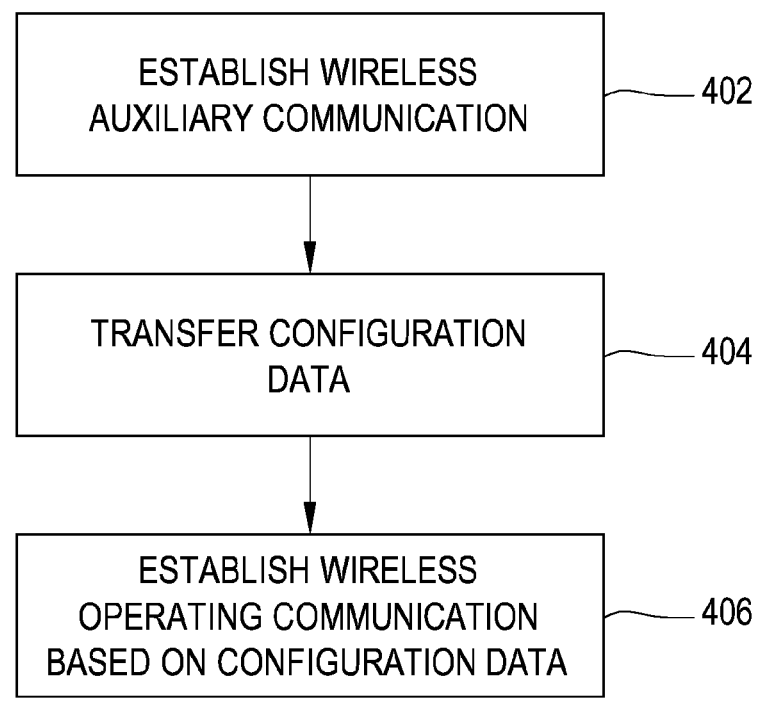
FIG. 4 is a block diagram showing the general process of establishing a wireless operating communication.

FIG. 4 is a block diagram showing the general process of establishing a wireless operating communication. In step 402, a wireless auxiliary communication between the blood treatment device and the medical accessory is established. In step 404, configuration data is transferred using the wireless auxiliary communication. In step 406, the wireless operating communication between the blood treatment device and the medical accessory is established, based on the configuration data.

The general process of establishing a wireless operating communication is based on the wireless auxiliary communication having a limited range that requires the accessory and device (more precisely, the data storage unit of the medical accessory and the data acquisition unit of the blood treatment device) to be in a pre-defined proximity or closer to each other. The motivation is to make this proximity a systematic requirement that cannot easily be adjusted or overcome by locally changing configuration parameters or adapting any one of the device and accessory. In contrast, it is desired that the accessory be brought into proximity to the device in order to ensure that the operating personnel can physically (e.g., visually) confirm the presence of both the accessory and the device, as well as their respective current status and configuration. Only if the accessory is within the pre-defined proximity of the device or closer, an attempt to establish data communication between the two entities can be initiated, because the wireless auxiliary communication is, by design, not capable of communication over distances longer than the pre-defined proximity. This is a strong requirement, which prevents users from mistakenly establishing data communication between devices and accessories not intended for being linked.

As such, the maximum operating distance of the wireless auxiliary communication is required to be shorter than the maximum operating distance of the wireless operating communication. Further, the wireless auxiliary communication has a pre-defined maximum operating distance, which is preferably configured not to be (easily) changeable by a user locally. In this manner, establishing a wireless operating communication between a device and an accessory is only possible if the accessory is within the maximum operating distance of the wireless auxiliary communication, whereas a safe and reliable wireless connection can be achieved by means of the wireless operating communication, because the maximum operating distance thereof is (much) longer than that of the wireless auxiliary communication.

Prior to establishing a wireless operating communication between the blood treatment device and the medical accessory, configuration data facilitating the wireless operating communication have to be set. It is known that generic networking devices typically comprise I/O means, which enable a user to enter the desired configuration data manually, for example providing WLAN access credentials and other parameters. According to the described process, the configuration data are transferred using a wireless auxiliary communication, wherein the configuration data contain the necessary data (which could be entered manually, see above) in a manner that allows for the device and accessory to establish a wireless operating communication between each other without further intervention of a user. Substantially at the same time of transferring the configuration data, presence of the medical accessory in proximity of the blood treatment device is ensured, because of the proximity being defined by the maximum operating distance of the wireless auxiliary communication.

In one example, the blood treatment device and the medical accessory are already in data communication with a same wireless data network (e.g. WLAN), without having established a data communication with each other (which would be required in order to transfer operating data between each other). In order to establish a wireless operating communication with each other, at least one of the device 10 and accessory 20 must be able to identify the other and parameters for establishing the operating communication have to be transferred.

Typically, the medical accessory provides configuration data that allow the blood treatment device to establish a wireless operating communication with the medical accessory and/or to determine a number of properties of the medical accessory.

The configuration data can comprise one or more of a Service Set Identifier (SSID), a channel number (e.g. 1 to 13) or operating frequency (or frequency range), a pre-shared key or other credentials necessary for establishing a wireless operating communication. In one example, the blood treatment device provides one or more of the above configuration data to the medical accessory, which subsequently can establish a wireless connection to a wireless network using the configuration data. Afterwards, a wireless operating communication can be established between the blood treatment device and the medical accessory, both of which are now linked to the same (wireless) network.

Additionally or alternatively, the configuration data can comprise an accessory id, an accessory type, an accessory status, an accessory configuration, etc. In some examples, an accessory id and/or accessory type can be used by the blood treatment device to identify a medical accessory and confirm that the medical accessory, with which a wireless operating communication is to be establishes, actually is suitable for operation with the blood treatment device. In some examples, the blood treatment device uses an accessory status (e.g. primed, unused, indicating proper operation, etc.) and/or an accessory configuration (e.g. configured and operating to measure blood pressure, oxygenation, etc.) in order to determine a proper status and/or configuration of the medical accessory. In all examples, if the blood treatment device determines that the medical accessory is not of the required type or lacks the required status and/or configuration, it is possible that the blood treatment device denies establishing a wireless operating communication.

In a second specific embodiment, the fluid processing medical apparatus is an infusion pump. All mentioned communication systems applies exactly to an infusion pump as well.

In detail the infusion pump may include, for example an intravenous fluid infusion pump. The pump may be clamped onto a standard IV pole. The pump includes a main body portion and at least one pump module portion. Of course, two ore more pump module portions may be provided. It is contemplated the use of any number of pumping modules depending on the requirements of the pump user. Formed at the upper periphery of the main body portion a carrying handle may be present. The main body further includes a liquid crystal display (LCD) area which is used to convey various information about the pump to the user and provides for user interface with the pump. The main body includes data-entry keys for inputting prescriptions or other data. The main body portion includes a slave microprocessor which is a slave to a master microprocessor. The slave microprocessor further includes an analog-to-digital converter (A/D converter). All microprocessors include software in read-only memory (ROM) which drives the user interaction and pump-monitoring functions.

The infusion pump may include a single module which is connected to or disconnected from the main body portion.

The pump module includes module housing, an upper module plate and a lower module plate. Fastening means are provided to secure the pump module to the main body. The fastening means include a plurality of extended bolts which extend through apertures defined in the lower module plate, the module housing and the upper module plate to threaded apertures defined on the bottom of the main body. Any number of pump modules can be added to the infusion pump by utilizing the appropriate fastening means. The pump module includes a microprocessor.

The pump modules are generally standard IV tube pump modules; use of alternative pump modules employing alternative pumping technology, such as for example, syringe pump modules is however contemplated. The pump module includes a tube-loading channel into which a standard IV tube is loaded into the pump. The pump module includes an automatic tube-loading feature. Contained within the tube-loading channel is a keyed slot adapted to receive a slide clamp contained on the IV tube. The pump module includes a free-flow prevention feature.

In the following, several typical usage scenarios for the method of establishing a wireless operating communication between a blood treatment device and a medical accessory are described. These examples are not limiting the scope of the disclosed method, but merely illustrate the possibilities for combining different technologies and processes.

Example 1

In the first example, a blood treatment device establishes a wireless operating communication via a LAN/WLAN network to a medical accessory having a QR-code attached thereto. The blood treatment machine has a wired connection to a local area network (LAN), which in turn is extended by one or more wireless access points providing a connection to the LAN to a number of WLAN devices and accessories. The medical accessory (e.g. a pressure cuff) is in data communication with the LAN via a WLAN through the aforementioned one or more access points, effectively, therefore, being in potential data communication with any device connected to the LAN or WLAN. The blood treatment device has an IP address (e.g. 10.129.10.18) assigned to it and the medical accessory also has an IP address (e.g. 10.129.10.16) assigned to it. The optical pattern is attached to the medical accessory in the form of a QR-code. The QR-code (i.e. the data storage unit) stores configuration data necessary for establishing the wireless operating communication.

Figure 5:
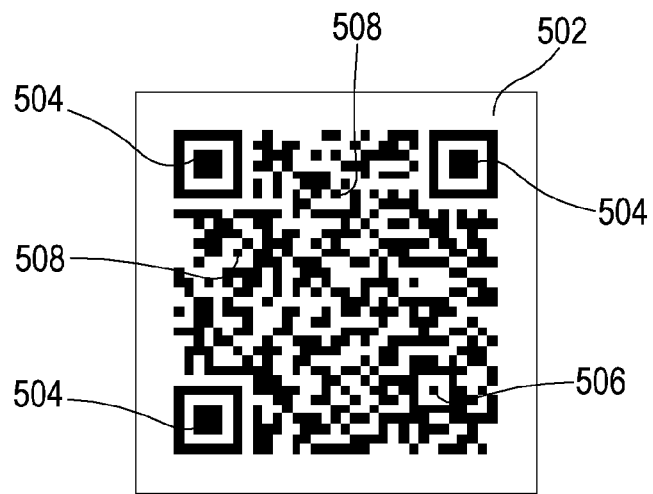
FIG. 5 shows an exemplary optical pattern in which configuration data is encoded.

FIG. 5 shows an exemplary optical pattern in which configuration data is encoded. The data encoded in the QR-code in this example is (annotation added):
id=54321 (accessory id; e.g. a numeric or text identifier)
ty=67890 (accessory type; e.g. a numeric or text identifier)
st=101 (accessory status; e.g. a numeric or text identifier)
cf=3 (accessory configuration; e.g. a numeric or text identifier)
ad=10.129.10.16 (accessory IPv4 address)
ek=6f2xCh872 (encryption key)

The QR-code shown in FIG. 5 is of the type "plain text". However, any suitable QR-code could be used to encode the configuration data. The QR-code can comprise one or more of the following elements: a "quiet" zone 502 around the QR-code, one or more finder patterns 504, one or more alignment patterns 506, timing patterns 508 running horizontally and vertically between the finder patterns (e.g. in the form of a line of alternating black and white dots running horizontally and vertically between the finder patterns), version information, data and error corrections code words, and a data encoding region.

Figure 6:
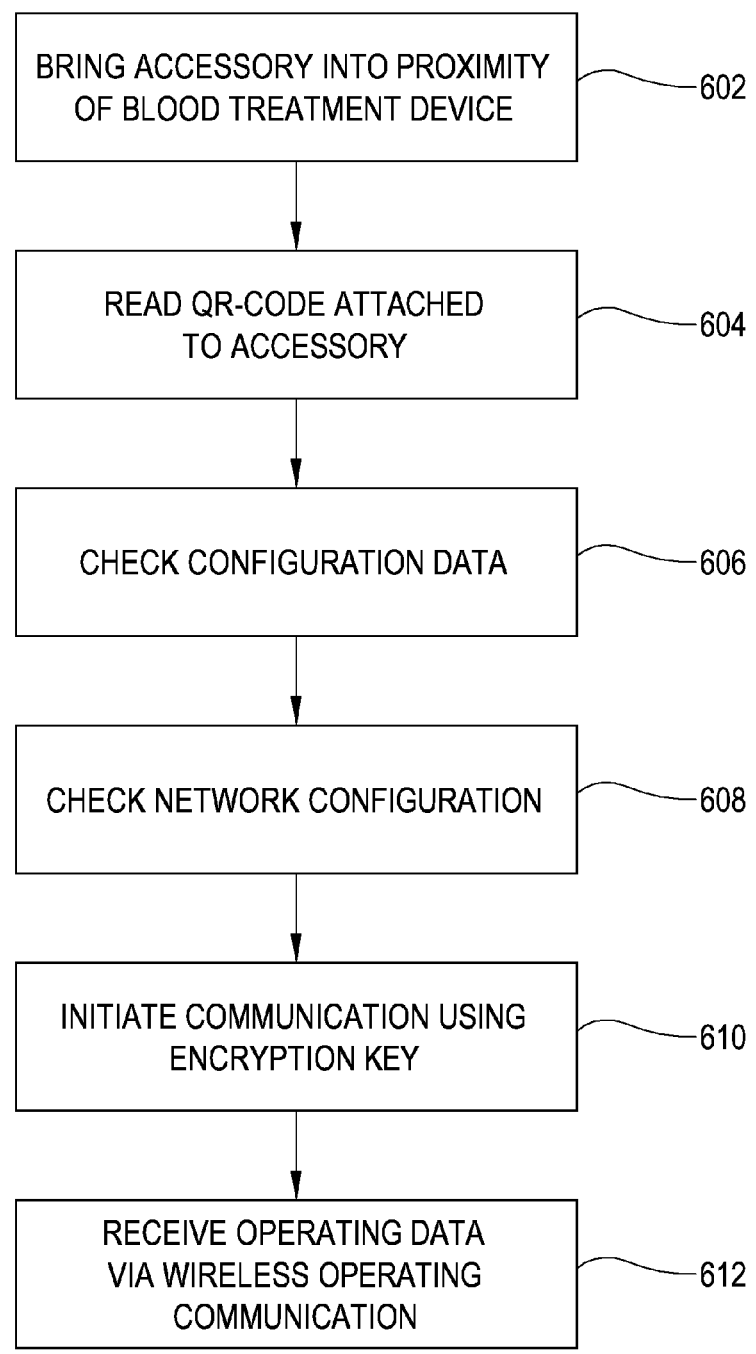
FIG. 6 shows the process of establishing a wireless operating communication between the device and accessory according to Example 1, FIG. 7 schematically shows an RFID unit in the form of an RFID tag that can be integrated into a medical accessory.

FIG. 6 shows the process of establishing a wireless operating communication between the device and accessory according to Example 1. In step 610 an operator brings the medical accessory into proximity of the blood treatment device, or, more precisely, brings the data storage unit of the medical accessory into proximity of the data acquisition unit of the blood treatment device. In this example, the QR-code attached to the accessory is brought into proximity to an optical scanner associated to the blood treatment device such that the optical scanner can scan the optical pattern making up the QR-code. In step 604 the optical scanner scans the optical pattern. This can be initiated either by the operator executing a scanning operation at the device or automatically by the device checking an image supplied by the scanner at regular intervals and automatically detecting the presence of a valid optical pattern within the field of view of the scanner. The scanned image is subsequently decoded in order to attain the configuration data listed above. Optionally, an optical and/or acoustic feedback signal is given by the device upon completion of the scanning and/or decoding. In step 606, the blood treatment device checks the configuration data. This check can be more or less extensive. First of all, a checksum (potentially present in the encoded data, but not listed above) can be computed in order to confirm the validity of the data and/or a correct scanning/decoding. Also, a plausibility check can be performed, where the configuration data are checked for any conflicting or otherwise obviously erroneous data. For example, it can be possible that the configuration data encoded in the QR-code attached to the accessory is outdated or contains implausible data. Any such problems can be checked during step 606. However, most importantly, the blood treatment device can check that the properties of the medical accessory, as encoded in the configuration data, indicate that the accessory has a valid id, and is of a type, status, and configuration suitable for operation with the blood treatment device. For example, even if a valid id and type are provided, the device can check if the accessory has the correct status (e.g. minimum remaining operational time left according to battery power, accessory properly attached to patient, etc.) and/or whether the accessory has a suitable configuration (e.g. configured to check a patient's blood pressure at the correct intervals; alternatively other blood parameters, etc.). Optionally, an optical and/or acoustic feedback signal is given by the device upon completion of checking of the configuration data. In step 608, the device checks whether a functioning data connection is available. This step can, for example, include checking a TCP/IP connection between the device and the IP address of the accessory as given in the configuration data (in Example 1, this can be done, e.g., via a network ping to the address 10.129.10.16). If the data connection is operational, the device can establish the wireless operating communication in step 610. Optionally, an optical and/or acoustic feedback signal is given by the device upon completion of the checking of the network configuration. In step 610, the device can, for example, use the encryption key supplied by the accessory in order to establish a secure communication (e.g. via secure sockets layer (SSL)) with the accessory, that is tamper-proof and prevents data being changed or read by other network devices. In this context, the term "encryption key" is used to refer to all kinds of suitable data encryption mechanisms, including symmetric and asymmetric encryption, regardless of the underlying protocols and/or mechanisms. It is understood that some encryption protocols require certificates, public/private keys, etc. in order to function properly. Optionally, an optical and/or acoustic feedback signal is given by the device upon completion of the establishing of the wireless operating communication. In step 612, the blood treatment device receives operating data (e.g. a patient's blood pressure measured by the pressure cuff) over the wireless operating communication.

Example 2

In the second example, a blood treatment device establishes a wireless operating communication via a LAN/WLAN network to a medical accessory capable of NFC. Example 2 is similar to the above-described Example 1 in that the network infrastructure and the general process of establishing the wireless operating communication are practically identical, except for the technical manner in which the configuration data are transmitted.

In Example 2, the medical accessory has an integrated RFID unit (e.g. an RFID tag or transponder) that stores the same configuration data as listed above in Example 1. An operator approaches the accessory to the device in a similar manner as in Example 1, but focuses on getting the data storage unit (i.e. the NFC unit; e.g. an RFID tag) of the medical accessory into proximity to the data acquisition unit (i.e. an NFC unit; e.g. an RFID reader) integrated into or otherwise associated to the blood treatment device. The device can automatically detect the presence of the accessory due to the RFID unit integrated therein being activated by the RFID reader of the device. The RFID reader of the device can then read the information stored on the RFID unit integrated into the accessory wirelessly and decode the configuration data in a suitable manner.

In some examples of RFID communication, two-way radio transceivers (transmitter-receiver units) called interrogators or readers send a signal to an RFID tag and read its response. RFID tags can be passive, active or battery-assisted passive. An active tag has an on-board battery and periodically transmits its ID signal. A battery-assisted passive RFID tag has a small battery on board and is activated when in the presence of an RFID reader. A passive tag is cheaper and smaller because it has no battery. However, to start operation of passive tags, they must be initially activated with a suitable electromagnetic power level stronger than for signal transmission. The described RFID tags are suitable for the scope of the present method, as are alternative RFID and/or NFC communication components and processed. Therefore, the above description of RFID tags is not intended as limiting.

Figure 7:
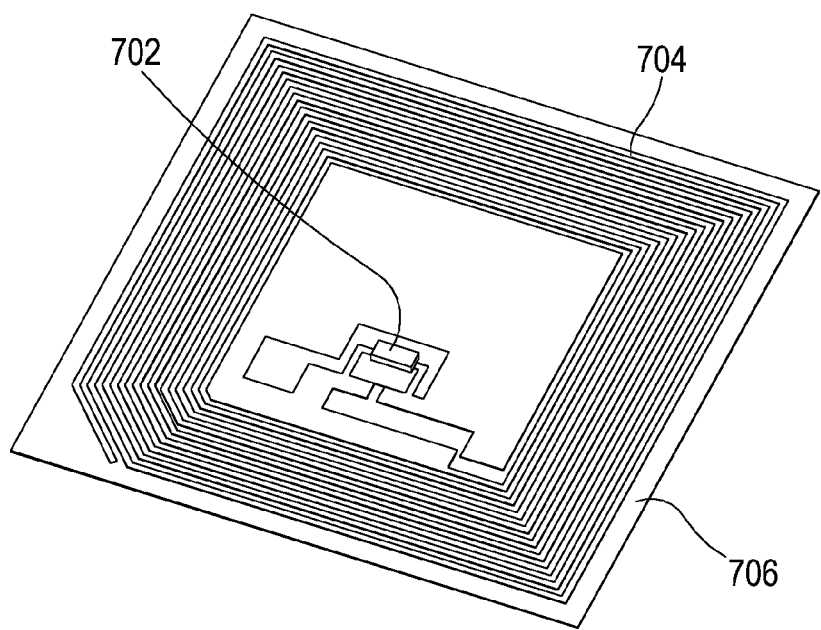

FIG. 7 schematically shows, as an example for a data storage unit, an RFID unit in the form of an RFID tag that can be integrated into a medical accessory. The RFID tag comprises an integrated circuit or micro-chip 702 which stores the information and handles the communication with other RFID units. Further, the RFID-tag comprises an antenna 704 and a substrate 706 (e.g. an adhesive film material). The RFID tag can be integrated into the medical accessory in a manner not directly visible from the outside (e.g. under a cover of some kind or generally within a housing). Alternatively, the RFID tag can be a common adhesive tag that can be affixed to a device on an outside surface thereof, which makes it very easy to equip existing medical accessories with NFC/RFID capabilities.

Except for the manner in which the configuration data are transmitted, the process steps in Example 2 are identical to those described above with respect to Example 1.

Example 3

In the third example, a blood treatment device establishes a wireless operating communication via an ad-hoc WLAN connection to a medical accessory. In this example, the configuration data can be transferred between the medical accessory and the blood treatment device in any suitable manner (e.g. as described above with respect to Example 1 and Example 2). However, the blood treatment device and the medical accessory are not connected to a common LAN/WLAN network, thus requiring an alternative means for communication. In this example, the device and accessory are each equipped with a wireless communication unit capable of establishing an ad-hoc (i.e. non "infrastructure") WLAN communication which basically consists of nodes forwarding data between one another without the need for dedicated infrastructure components (e.g. routers, access points, wired networks, etc.). In order to establish an ad-hoc network, for example, the device can provide the necessary network configuration including an SSID, private IP address range, etc. The accessory can then receive the corresponding configuration data from the device in order establish the wireless (ad-hoc) operating communication. The general setup is shown in FIG. 3 as already described above. While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:
1. A method of establishing a wireless operating communication between a fluid processing medical device and a medical accessory, the method comprising:
 establishing a wireless auxiliary communication between the fluid processing medical device and the medical accessory;
 transferring configuration data using the wireless auxiliary communication; and establishing a wireless operating communication between the fluid processing medical device and the medical accessory based on the configuration data, wherein a maximum operating distance of the wireless auxiliary communication is shorter than a maximum operating distance of the wireless operating communication;

wherein, after the wireless operating communication has been established, the method further comprises:

establishing a second wireless auxiliary communication between the fluid processing medical device and a second medical accessory;

transferring second configuration data using the second wireless auxiliary communication;

determining whether the medical accessory and the second medical accessory are of a same type based on the configuration data and the second configuration data; and if the medical accessory and the second medical accessory are of the same type:
  inhibiting data communication using the wireless operating communication with the second medical accessory; and
  closing the second wireless auxiliary communication.

2. The method of claim 1, wherein the maximum operating distance of the wireless auxiliary communication is less than 2 meters and the maximum operating distance of the wireless operating communication is greater than 2 meters.

3. The method of claim 2, wherein the maximum operating distance of the wireless auxiliary communication is less than 20 centimeters and the maximum operating distance of the wireless operating communication is greater than 10 meters.

4. The method of claim 1, wherein establishing the wireless operating communication further comprises:
  determining, based on the configuration data, communication data of the medical accessory to operate with the wireless operating communication, wherein the communication data is indicative of a communication configuration of the medical accessory, wherein the configuration data comprise type data indicative of a plurality of properties of the medical accessory;
  initiating, based on the communication data, a data communication between the fluid processing medical device and the medical accessory using the wireless operating communication.

5. The method of claim 4, wherein establishing the wireless operating communication further comprises:
  determining, based on the type data, whether the medical accessory is of a type suitable to operate with the fluid processing medical device; and
  closing both the wireless auxiliary communication and the wireless operating communication with the medical accessory if the medical accessory is not of a type suitable for operation with the fluid processing medical device, wherein the plurality of properties of the medical accessory that the type data are indicative of comprise one or more of:
  hardware data indicative of a hardware configuration of the medical accessory;
  software data indicative of a software configuration of the medical accessory; and
  firmware data indicative of a firmware configuration of the medical accessory, and wherein determining whether the medical accessory is of a type suitable to operate with the fluid processing medical device is based on one or more of the hardware data, the software data, and the firmware data.

6. The method of claim 1, wherein, after the wireless operating communication has been established, the method further comprises:
  comparing an idle time interval indicative of a time interval since the last data communication between the fluid processing medical device and the medical accessory using the wireless operating communication with a pre-defined maximum idle time interval;
  closing the wireless operating communication if the idle time interval is greater than the pre-defined maximum idle time interval; and
  performing an alarm procedure if the idle time interval is greater than the pre-defined maximum idle time interval.

7. The method of claim 1, wherein establishing the wireless auxiliary communication is preceded by bringing a data storage unit of the medical accessory into a close proximity of a data acquisition unit of the fluid processing medical device in order to initiate the establishing of the wireless auxiliary communication, the close proximity being equal to or shorter than the maximum operating distance of the wireless auxiliary communication, the medical accessory and the fluid processing medical device establishing said wireless auxiliary communication when the data storage unit is in the close proximity of the data acquisition unit.

8. The method of claim 7, wherein the data storage unit of the medical accessory comprises an optical bar-code or an optical matrix code, and wherein the data acquisition unit of the fluid processing medical device comprises an optical reader configured to read the optical bar code or the optical matrix code.

9. The method of claim 7, wherein the data storage unit of the medical accessory comprises a near field communication unit, the near field communication unit comprising a near field communication transmitter and receiver, and
  wherein the data acquisition unit of the fluid processing medical device comprises a near field communication reader configured to read data from the near field communication transmitter and receiver.

10. The method of claim 7, wherein establishing the wireless auxiliary connection comprises:
  detecting the presence of the data storage unit of the medical accessory within an initial distance to the data acquisition unit of the fluid processing medical device, the initial distance being equal to or shorter than the maximum operating distance of the wireless auxiliary communication,
  the method further comprising closing the wireless auxiliary communication after the configuration data has been transferred.

11. The method of claim 1, wherein the wireless operating communication operates at a maximum bandwidth higher than a maximum bandwidth of the wireless auxiliary communication on a wireless frequency range different from a wireless frequency range of the wireless auxiliary communication according to a wireless network protocol different from a wireless network protocol of the wireless auxiliary communication.

12. The method of claim 11, wherein the wireless frequency range of the wireless auxiliary communication comprises one or more of:
  a visible or near infra-red optical frequency range, and
  a microwave frequency range, and
  wherein the wireless frequency range of the operating communication comprises one or more of:

from about 868 MHz to about 868.6 megahertz,
from about 902 MHz to about 928 megahertz,
from about 2.4 GHz to about 2,485 gigahertz, and
from about 5,150 GHz to about 5,850 gigahertz; and
wherein the wireless auxiliary communication is based on at least one of:
near field communication, and
optical recognition; and
wherein the wireless operating communication is based on at least one of:
wireless local area network, and
BLUETOOTH.

13. The method of claim 12, wherein detecting the presence of the data storage unit of the medical accessory within the initial distance comprises:
scanning an optical pattern visibly attached to the medical accessory; and
decoding the configuration data from the optical pattern.

14. The method of claim 12, wherein detecting the presence of the data storage unit of the medical accessory within the initial distance comprises:
sending an electromagnetic signal from the data acquisition unit of the fluid processing medical device to the data storage unit of the medical accessory to initiate the wireless auxiliary communication, the electromagnetic signal sent in order to supply energy to a transponder or transceiver comprised in the data storage unit of the medical accessory; and
receiving the configuration data using the wireless auxiliary communication in response to the electromagnetic signal.

15. The method of claim 1 comprising:
connecting the medical accessory to a patient;
generating, at the medical accessory, treatment data based on one or more physical characteristics of the patient, the one or more physical characteristics measured using the medical accessory; and
transferring the treatment data to the fluid processing medical device using the wireless operating communication, the treatment data comprising one or more values of the one or more physical characteristics of the patient, the one or more physical characteristics selected from a group consisting of:
patient's blood pressure,
patient's weight,
patient's temperature,
patient's heart rate,
patient's oxygen saturation in blood, and
blood leakage of patient's blood in correspondence of a vascular access,
wherein the medical accessory is connected to the patient after the configuration data has been transferred.

16. An extracorporeal blood treatment device comprising:
a blood treatment unit comprising a blood chamber and a fluid chamber separated from the blood chamber by a semipermeable membrane;
an extracorporeal blood circuit comprising an arterial line for blood removal from an individual and a venous line for blood return to the individual, the arterial line connected to an inlet and the venous line connected to an outlet of the blood chamber;
a blood moving device to move the blood along the extracorporeal circuit;
a fluid circuit comprising at least a discharge line connected to an outlet of the fluid chamber;
an ultrafiltration device to ultrafilter plasmatic liquid from the blood chamber to the fluid chamber across the semipermeable membrane;
a device control unit configured to perform:
establishing a wireless auxiliary communication between the blood treatment device and a medical accessory;
transferring configuration data using the wireless auxiliary communication; and
establishing a wireless operating communication between the blood treatment device and the medical accessory based on the configuration data, wherein a maximum operating distance of the wireless auxiliary communication is shorter than a maximum operating distance of the wireless operating communication,
a support structure supporting at least the ultrafiltration device and the blood moving device,
a plurality of replaceable components of different categories engaged to the support structure in correspondence of respective operating areas, each component of a same category comprising a respective mechanical connection to a corresponding operating area on the support structure different from that of components of other categories, wherein said support structure includes a plurality of different types of engaging means, each type of engaging means being designed for mechanically engaging, in a respective operating area, a component of one corresponding category only,
at least a user interface enabling setting of a plurality of parameters pertinent to operation of said extracorporeal blood treatment device or pertinent to a process to be performed by said extracorporeal blood treatment device, the user interface including at least a screen,
wherein the wireless reader comprises a reading portion to read information concerning the components, the reading portion being spaced from said operating areas and accessible to read the information irrespective of the components engaged or not engaged to the support structure,
wherein the device control unit of the blood treatment device controls operation of said blood treatment device and is responsive to actions by a user on said user interface, said device control unit also communicating with the wireless reader and programmed to receive and store at least said information concerning the components every time the wireless reader reads information concerning a new component installed or to be installed on the structure.

17. The extracorporeal blood treatment device of claim 16, wherein the maximum operating distance of the wireless auxiliary communication is less than 20 centimeters, and wherein the maximum operating distance of the wireless operating communication is greater than 10 meters.

18. The extracorporeal blood treatment device of claim 16, wherein establishing the wireless operating communication further comprises:
determining, based on the configuration data, communication data of the medical accessory, the communication data of the medical accessory configured to operate with the wireless operating communication, wherein the communication data is indicative of a communication configuration of the medical accessory, wherein the configuration data comprises type data indicative of a plurality of properties of the medical accessory;

initiating, based on the communication data, a data communication between the blood treatment device and the medical accessory using the wireless operating communication.

19. The extracorporeal blood treatment device of claim 16, wherein establishing the wireless auxiliary communication is preceded bringing a data storage unit of the medical accessory into a close proximity of a data acquisition unit of the blood treatment device in order to initiate the establishing of the wireless auxiliary communication, the close proximity being equal to or shorter than the maximum operating distance of the wireless auxiliary communication, the medical accessory and the blood treatment device establishing said wireless auxiliary communication when the data storage unit is in the close proximity of the data acquisition unit, wherein the device control unit is further configured to execute closing the wireless auxiliary communication after the configuration data has been transferred.

20. The extracorporeal blood treatment device of claim 16, wherein the accessory control unit is configured to perform inhibiting data communication with a second blood treatment device over the wireless operating communication until the wireless operating communication with the blood treatment device is closed.

21. The extracorporeal blood treatment device of claim 16, wherein the medical accessory is configured to be connected to any one of a number of a plurality of blood treatment devices, the medical accessory configured to be not connectable to any one of a number of a plurality of medical accessories, the medical accessory comprising a transmitter to transmit wireless signals over a wireless operating communication, wherein the medical accessory further comprises a receiver to receive wireless signals over a wireless operating communication, and wherein the blood treatment device comprises a receiver to receive wireless signals over a wireless operating communication, wherein the blood treatment device further comprises a transmitter to transmit wireless signals over a wireless operating communication.

22. The extracorporeal blood treatment device of claim 16, wherein the medical accessory comprises a wireless reader to read data on an information carrier of a component installed or to be installed on the blood treatment device, wherein the wireless reader comprises an optical reader or a radio-frequency reader to detect said data on the information carrier of the component when the component and the wireless reader are approached to one another at a distance less then 30 cm.

23. A method of establishing a wireless operating communication between a fluid processing medical device and a medical accessory, the method comprising:
  establishing a wireless auxiliary communication between the fluid processing medical device and the medical accessory;
  transferring configuration data using the wireless auxiliary communication; and
  establishing a wireless operating communication between the fluid processing medical device and the medical accessory based on the configuration data, wherein a maximum operating distance of the wireless auxiliary communication is shorter than a maximum operating distance of the wireless operating communication,
  wherein establishing the wireless operating communication comprises:
  determining, based on the configuration data, communication data of the medical accessory to operate with the wireless operating communication, wherein the communication data is indicative of a communication configuration of the medical accessory, wherein the configuration data comprise type data indicative of a plurality of properties of the medical accessory;
  initiating, based on the communication data, a data communication between the fluid processing medical device and the medical accessory using the wireless operating communication;
  determining, based on the type data, whether the medical accessory is of a type suitable to operate with the fluid processing medical device; and
  closing both the wireless auxiliary communication and the wireless operating communication with the medical accessory if the medical accessory is not of a type suitable for operation with the fluid processing medical device, wherein the plurality of properties of the medical accessory that the type data are indicative of comprise one or more of:
  hardware data indicative of a hardware configuration of the medical accessory;
  software data indicative of a software configuration of the medical accessory; and
  firmware data indicative of a firmware configuration of the medical accessory, and wherein determining whether the medical accessory is of a type suitable to operate with the fluid processing medical device is based on one or more of the hardware data, the software data, and the firmware data.

24. The method of claim 23, wherein the maximum operating distance of the wireless auxiliary communication is less than 2 meters and the maximum operating distance of the wireless operating communication is greater than 2 meters.

25. The method of claim 24, wherein the maximum operating distance of the wireless auxiliary communication is less than 20 centimeters and the maximum operating distance of the wireless operating communication is greater than 10 meters.

26. The method of claim 23, wherein, after the wireless operating communication has been established, the method further comprises:
  comparing an idle time interval indicative of a time interval since the last data communication between the fluid processing medical device and the medical accessory using the wireless operating communication with a pre-defined maximum idle time interval;
  closing the wireless operating communication if the idle time interval is greater than the pre-defined maximum idle time interval; and
  performing an alarm procedure if the idle time interval is greater than the pre-defined maximum idle time interval.

27. The method of claim 23, wherein establishing the wireless auxiliary communication is preceded by bringing a data storage unit of the medical accessory into a close proximity of a data acquisition unit of the fluid processing medical device in order to initiate the establishing of the wireless auxiliary communication, the close proximity being equal to or shorter than the maximum operating distance of the wireless auxiliary communication, the medical accessory and the fluid processing medical device establishing said wireless auxiliary communication when the data storage unit is in the close proximity of the data acquisition unit.

28. The method of claim 27, wherein the data storage unit of the medical accessory comprises an optical bar-code or an optical matrix code, and wherein the data acquisition unit of the fluid processing medical device comprises an optical reader configured to read the optical bar code or the optical matrix code.

29. The method of claim 27, wherein the data storage unit of the medical accessory comprises a near field communication unit, the near field communication unit comprising a near field communication transmitter and receiver, and
wherein the data acquisition unit of the fluid processing medical device comprises a near field communication reader configured to read data from the near field communication transmitter and receiver.

30. The method of claim 27, wherein establishing the wireless auxiliary connection comprises:
detecting the presence of the data storage unit of the medical accessory within an initial distance to the data acquisition unit of the fluid processing medical device, the initial distance being equal to or shorter than the maximum operating distance of the wireless auxiliary communication,
the method further comprising closing the wireless auxiliary communication after the configuration data has been transferred.

31. The method of claim 23, wherein the wireless operating communication operates at a maximum bandwidth higher than a maximum bandwidth of the wireless auxiliary communication on a wireless frequency range different from a wireless frequency range of the wireless auxiliary communication according to a wireless network protocol different from a wireless network protocol of the wireless auxiliary communication.

32. The method of claim 31, wherein the wireless frequency range of the wireless auxiliary communication comprises one or more of:
a visible or near infra-red optical frequency range, and
a microwave frequency range, and
wherein the wireless frequency range of the operating communication comprises one or more of:
from about 868 MHz to about 868.6 megahertz,
from about 902 MHz to about 928 megahertz,
from about 2.4 GHz to about 2,485 gigahertz, and
from about 5,150 GHz to about 5,850 gigahertz; and
wherein the wireless auxiliary communication is based on at least one of:
near field communication, and
optical recognition; and wherein the wireless operating communication is based on at least one of:
wireless local area network, and
BLUETOOTH.

33. The method of claim 32, wherein detecting the presence of the data storage unit of the medical accessory within the initial distance comprises:
scanning an optical pattern visibly attached to the medical accessory; and
decoding the configuration data from the optical pattern.

34. The method of claim 32, wherein detecting the presence of the data storage unit of the medical accessory within the initial distance comprises:
sending an electromagnetic signal from the data acquisition unit of the fluid processing medical device to the data storage unit of the medical accessory to initiate the wireless auxiliary communication, the electromagnetic signal sent in order to supply energy to a transponder or transceiver comprised in the data storage unit of the medical accessory; and
receiving the configuration data using the wireless auxiliary communication in response to the electromagnetic signal.

35. The method of claim 23 comprising:
connecting the medical accessory to a patient;
generating, at the medical accessory, treatment data based on one or more physical characteristics of the patient, the one or more physical characteristics measured using the medical accessory; and
transferring the treatment data to the fluid processing medical device using the wireless operating communication, the treatment data comprising one or more values of the one or more physical characteristics of the patient, the one or more physical characteristics selected from a group consisting of:
patient's blood pressure,
patient's weight,
patient's temperature,
patient's heart rate,
patient's oxygen saturation in blood, and
blood leakage of patient's blood in correspondence of a vascular access,
wherein the medical accessory is connected to the patient after the configuration data has been transferred.

* * * * *